US00PP17750P2

(12) United States Plant Patent
Bradford

(10) Patent No.: US PP17,750 P2
(45) Date of Patent: May 22, 2007

(54) PEACH TREE NAMED 'SPRING PRINCESS'

(50) Latin Name: *Prunus persica*
Varietal Denomination: Spring Princess

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/311,233

(22) Filed: Dec. 20, 2005

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP7,953 P 8/1992 Bradford
PP13,352 P2 * 12/2002 Sherman ..... Plt./197
PP14,535 P3 * 2/2004 Lopez ..... Plt./197
PP14,769 P3 * 5/2004 Lopez ..... Plt./197
2003/0079262 P1 * 4/2003 Lopez ..... Plt./197
2003/0088896 P1 * 5/2003 Lopez ..... Plt./197

* cited by examiner

*Primary Examiner*—Wendy C. Haas

(57) ABSTRACT

The present invention relates to a peach tree, *Prunus persica,* and more particularly to a new and distinct variety characterized by a medium size, vigorous, half-hardy, self-fertile, productive and regular bearing tree. The fruit matures under the ecological conditions described in late May, with first picking on May 24, 2005. The fruit is very large in size, sweet and acidic in flavor, somewhat oblate in shape, clingstone in type, yellow in flesh color, mostly red in skin color, and melting in texture. The present variety was the result of an open pollinated unnamed peach (unpatented) seedling.

1 Drawing Sheet

Botanical classification: *Prunus persica.*
Variety denomination: 'Spring Princess'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seedlings each year of these fruits, usually to reveal recessive characteristics. The present invention relates to a new and distinct variety of peach tree, which has been demonstrated varietally as 'Spring Princess'.

During the spring of 1998 I gathered open pollinated seeds from several unnamed peaches (unpatented) located in my experimental orchard at Bradford Farms near Le Grand, Calif. in Merced County (San Joaquin Valley). Using embryoculture techniques I germinated the seeds, grew them as seedlings on their own root in my greenhouse, and transplanted them the following winter into a cultivated area of the experimental orchard described above as a group labeled "Early Peach (OP)". During the spring of 2002 I selected the present variety as a single seedling from this "Early Peach (OP)" group. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to 'Crimson Lady' (U.S. Plant Pat. No. 7,953) peach by producing good tasting fruit that is clingstone in type, mostly red skin color, and yellow in flesh color, but is distinguished therefrom by requiring considerably less chilling hours and by producing fruit that is larger in size, flatter in shape, melting instead of in non-melting in texture, and that matures about eight days earlier.

SUMMARY OF VARIETY

In summary, the present variety is characterized by a medium size, vigorous, half-hardy, self-fertile, productive and regular bearing tree. The fruit matures under the ecological conditions described in late May, with first picking on May 24, 2005. The fruit is very large in size, sweet and acidic in flavor, compressed axially in shape, clingstone in type, yellow in flesh color, mostly red in skin color, and melting in texture. The present variety was the result of an open pollinated unnamed peach seedling.

DRAWING

The accompanying photograph exhibits four whole fruits positioned to display the characteristics of the skin color and form, one fruit divided transversely to the suture plane to reveal the flesh and stone, typical leaves, and an inset of buds and flowers at various stages.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on May 26, 2005, on the original tree during its seventh growing season. All major color code designations are by reference to the Inter-Society Color Council, National Bureau of Standards. Common color names are also used occasionally.

Tree

Size: Medium, reaching a height of 12' [3.7 m.] and a spread of 10' [3.0 m.] after seven growing seasons utilizing typical dormant pruning.

Vigor: Vigorous, responding typically to irrigation and fertilization. The variety grows about 3' [0.9 m.] of surplus top-growth during the spring and summer. The plant should be grown on a standard commercial rootstock for production purposes.

Growth: Upright and dense.

Form: Pruned to be vase formed.

Hardiness: Half hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximately chilling requirement: 250 hours.

Trunk:

*Size.*—Medium, with a maximum diameter of 5" [127 mm.] after the seventh growing season.

*Texture.*—Shaggy.

*Bark color.*—A variegation of Dark grayish brown [62. d.gy.Br] and Dark grayish reddish brown [47. d.gy.rBr].

*Lenticels.*—Approximate Number Per Square Inch: 10. Color: Dark orange yellow [72. d.OY]. Average Size: 3/16" [4.8 mm.] to 7/16" [11.1 mm.]. Shape: Eye-shaped to elongated.

Branches:

*Size.*—Diameter of limb is 3¼" [82.6 mm.] measured 12" above the crotch and 2½" [64 mm.] measured 12" above the first fork.

*Texture.*—Smooth on 1st year wood, increasing roughness with age.

*Color.*—1st Year Wood Topside: Grayish red [19. gy.R]. 1st Year Wood Underside: Strong yellow green [117. s.YG]. Older Wood: Deep yellowish brown [75. deep yBr].

*Lenticels.*—Approximate Number Per Square Inch: More than 50 on second year wood. Color: Dark orange yellow [72. d.OY]. Typical size: 1/32" [0.8 mm.] to 3/16" [4.8]. Shape: Eye-shaped to elongated.

Leaves:

*Size.*—Medium. Average Length: 6" [152 mm.]. Average width: 1½" [38 mm.].

*Arrangement.*—Alternate.

*Thickness.*—Medium.

*Form.*—Elliptical.

*Apex.*—Acuminate.

*Base.*—Acute to rounded.

*Surface.*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Petiole.*—Average Length: 7/16" [11.1 mm.]. Average Thickness: 1/16" [1.6 mm.]. Color: Strong yellow green [117. s.YG].

*Stipules.*—Number: 2 to 6 per growing tip. Average Length: 3/8" [9.5 mm.]. Color: Strong yellow green [117. s.YG] becoming Dark grayish reddish brown [47. d.gy.rBr] with age when dried.

*Glands.*—Number: Usually 2 or 3. Position: First two alternate on petiole, rest on base of blade. Size: Small. Form: Globose. Color: Brilliant yellow green [116. brill.YG] with an increasing amount of Deep yellowish brown [75. deep yBr] toward the center with age.

*Leaf buds.*—Medium, pointed.

Flower buds:

*Hardiness.*—Half-hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with double blossoms rarely observed.

*Petal shape.*—Circular to oval.

*Petal margin.*—Somewhat wavy.

*Average petal diameter.*—¾" [19.1 mm.].

*Average petal length.*—¾" [19.1 mm.].

*Petal apex.*—Rounded.

*Petal base.*—Rounded to somewhat truncate.

*Petal color.*—Pale pink [7. p.Pk] toward the apex, Pale purplish pink [252. p.pPk] toward the base.

*Anther color.*—Moderate reddish orange [37. m.rO] over Light yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—⅝" [15.9 mm.].

*Fragrance.*—Moderate.

*Blooming period.*—Very early compared with other varieties.

*Onset of bloom.*—One percent on Feb. 3, 2005.

*Date of full bloom.*—Feb. 10, 2005.

*Duration of bloom.*—One to two weeks, dependent on ambient temperature.

*Number per cluster.*—1 to 3 with single flowers most common.

FRUIT

Maturity when described: Firm ripe, May 26, 2005.

Date of first picking: May 24, 2005.

Date of last picking: Jun. 1, 2005.

Size: Uniform, very large.
*Average diameter axially.*—2 11/16" [68.3 mm.].
*Average diameter across suture plane.*—3 1/8" [79.4 mm.].
*Typical weight.*—8.3 ounces [236 grams].
Form: Uniform, symmetrical.
*Longitudinal section form.*—Elliptical.
*Axial view.*—Round.
Suture: A moderately sharp groove near the base, shallower along the sides, and deeper and quite sharp near the apex, extending from the base to about 1" [25.4 mm.] beyond the pistil point, totally depressed.
Ventral surface: Rounded, lipped toward apex on both sides.
Lips: Equal.
Cavity: Flaring, elongated in the suture plane, suture showing on one side, Light yellow [86. l.Y] stem markings typical.
*Depth.*—9/16" [14.3 mm.].
*Breadth.*—1 1/4" [31.8 mm.].
Base: Truncate, but somewhat cordate if viewed parallel to the suture.
Apex: Truncate, but very cordate if viewed parallel to the suture.
Pistil point: Apical, negligible in length, very depressed within the suture.
Stem: Medium.
*Average length.*—7/16" [11.1 mm.].
*Average width.*—3/16" [4.8 mm.].
Skin:
*Thickness.*—Medium, tough.
*Surface.*—Medium.
*Tenacity.*—Tenacious to flesh.
*Astringency.*—Slightly astringent.
*Tendency to crack.*—Some in wet season.
*Color.*—Very deep red [14. v.deep R] mottled into Moderate reddish orange [37. m.rO] along the sides blending into Moderate orange yellow [71. m.OY] toward base.
Down: Moderate, short in length, does not roll up when rubbed.
Flesh:
*Color.*—Brilliant Yellow [83. brill.Y] with very slight Moderate red [15. m.R] flecking.
*Surface of pit cavity.*—Clingstone, Light yellow [86. l.Y] broken fibers when twisted from the stone.
*Amygdalin.*—Moderate, scarce.
*Juice.*—Abundant, watery.
*Texture.*—Medium firm, tough and melting.
*Fibers.*—Abundant, fine and tender.
*Ripens.*—Earliest at the apex.
*Flavor.*—Mildly acidic with pronounced peach flavor averaging 12 brix.
*Aroma.*—Moderate.
*Eating quality.*—Very good.

STONE

Type: Clingstone.
Form: Globose.
Hilum: Narrow, oblong.
Base: Straight.
Apex: Acute, with hooked tip 1/8" [3.2 mm.] in length and an average tip angle of 40 degrees.
Sides: Equal.
Surface: Vertical furrows along dorsal and ventral edge, pitted throughout.
Ridges: Very few, jagged toward the base.
External color: Light orange yellow [70. l.OY].
Internal color when cracked: Pale orange yellow [73. p.OY].
Cavity surface color: Light orange yellow [70. l.OY].
Average pit wall thickness: 7/32" [5.6 mm.].
Average width: 1 1/8" [28.6 mm.].
Average length: 1 3/8" [34.9 mm.].
Average breadth: 7/8" [22.2 mm.].
Tendency to split: Slight.
Kernel:
*Form.*—Oval.
*Pellicle color.*—Light yellowish brown [76. l.yBr].
*Skin color.*—Pale yellow [89. p.Y].
*Vein color.*—Light yellowish brown [76. l.yBr] when distinguishable.
*Taste.*—Sweet.
*Viable.*—Only by using embryoculture techniques.
*Average width.*—7/16" [11.1 mm.].
*Average length.*—3/4" [19.1 mm.].
*Amygdalin.*—Scant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Crimson Lady' (U.S. Plant Pat. No. 7,953) peach by producing good tasting fruit that is clingstone in type, mostly red skin color, and yellow in flesh color, but is distinguished therefrom by requiring considerably less chilling hours and by producing fruit that is larger in size, flatter in shape, melting instead of in non-melting in texture, and that matures about eight days earlier.

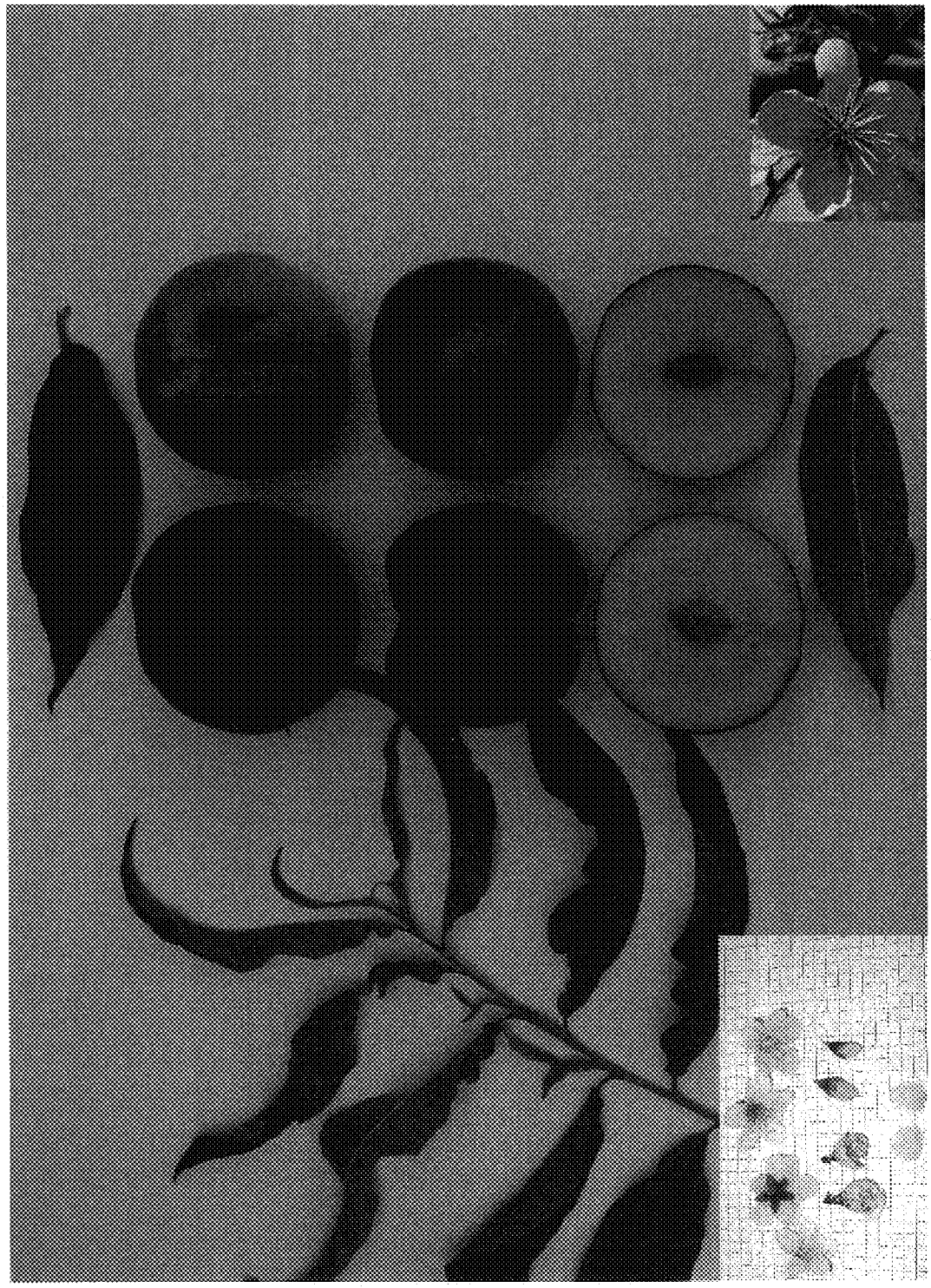

* * * * *